United States Patent
Katsuyama et al.

(10) Patent No.: US 6,171,580 B1
(45) Date of Patent: Jan. 9, 2001

(54) ULTRAVIOLET-SCREENING ZINC OXIDE EXCELLENT IN TRANSPARENCY AND COMPOSITION CONTAINING THE SAME

(75) Inventors: Tomoyuki Katsuyama; Asa Kimura, both of Kanagawa (JP)

(73) Assignee: Shiseido Company Ltd., Tokyo (JP)

( * ) Notice: Under 35 U.S.C. 154(b), the term of this patent shall be extended for 0 days.

(21) Appl. No.: 09/341,145

(22) PCT Filed: Nov. 17, 1998

(86) PCT No.: PCT/JP98/05165

§ 371 Date: Jul. 16, 1999

§ 102(e) Date: Jul. 16, 1999

(87) PCT Pub. No.: WO99/25654

PCT Pub. Date: May 27, 1999

(30) Foreign Application Priority Data

Nov. 18, 1997 (JP) .................................................... 9-333478
Dec. 17, 1997 (JP) .................................................... 9-364053

(51) Int. Cl.⁷ ................ A61K 7/42; A61K 7/44; A61K 7/00; C01G 9/02

(52) U.S. Cl. .................. 424/59; 423/622; 424/60; 424/400; 424/401

(58) Field of Search .................... 424/59, 60, 400, 424/401; 423/622

(56) References Cited

U.S. PATENT DOCUMENTS 5,527,519 * 6/1996 Miksits et al. ........................ 423/622
5,744,126 * 4/1998 Horino et al. ......................... 424/59

* cited by examiner

*Primary Examiner*—Shelley A. Dodson
(74) *Attorney, Agent, or Firm*—Townsend & Banta

(57) ABSTRACT

The present inventors conducted investigations in order to develop a metal oxide which enables effective UV-screening; i.e. which has excellent screening ability against ultraviolet rays, particularly against long-wavelength ultraviolet rays, as well as excellent visible-light transmission; and to provide a UV-screening composition that contains the metal oxide and can be applied to external use. As a result, the present inventors have found that zinc oxide produced by a particular method has a characteristic form; i.e., primary particles having an average particle diameter of 50–100 nm aggregate in a planer shape, and a ratio represented by $\ln T_{360nm}/\ln T_{400nm}$ ($T_{xnm}$: transmittance of transmitted light of X nm) of 10 or more, and exerts excellent screening effect against long-wavelength ultraviolet rays as well as excellent visible-light transmission. The present invention has been accomplished based on this finding. The zinc oxide of the present invention effectively exerts the above-described excellent characteristics; i.e. UV-screening effect and transparency, and can be applied to a composition for external use such as make-up cosmetics or sunscreen cosmetics.

38 Claims, 5 Drawing Sheets

ULTRAVIOLET-SCREENING ZINC OXIDE EXCELLENT IN TRANSPARENCY AND COMPOSITION CONTAINING THE SAME

TECHNICAL FIELD

The present invention relates to zinc oxide exhibiting an excellent screening effect, particularly against long-wavelength ultraviolet rays (UV-A), as well as to a composition containing the zinc oxide.

More particularly, the present invention relates to zinc oxide in the form of primary particles having an average particle diameter of 50–100 nm and forming a planar shape, which zinc oxide exerts an excellent screening effect against ultraviolet(UV) rays, particularly against long-wavelength UV rays, and excellent visible-light transmission. The present invention also relates to a UV-screening composition containing the zinc oxide and applicable to, e.g., a composition for external use.

BACKGROUND ART

Recently, adverse effects on the human body of ultraviolet rays included in sunlight have become widely known, and various measures directed toward alleviating or preventing the adverse effects have been considered.

Ultraviolet rays are divided into three categories based on dermatological effects, i.e., long-wavelength ultraviolet rays (UV-A) (320–400 nm), medium-wavelength ultraviolet rays (UV-B) (290–320 nm), and short-wavelength ultraviolet rays (UV-C) (shorter than 290 nm).

Of these, UV-C can cause fatal harm to living things, including human beings. So far, UV-C has been absorbed by the ozone layer of the upper atmosphere before reaching the earth (However, there is concern that recent depletion of the ozone layer may allow UV-C to damage living things on the earth).

UV-A and UV-B reach the earth, and human beings are exposed to them. UV-A and UV-B have a number of effects on the human body.

UV-A and UV-B have many more adverse effects rather than beneficial effects, such as promotion of production of vitamin D in the body.

The development of agents for preventing harm caused by UV-B started earlier and was carried out more actively than that for preventing harm caused by UV-A. However, adverse effects caused by UV-A, such as accelerated aging of the skin, have been noted recently, and a number of measures to effectively screen UV-A have been proposed.

Presently, when an inorganic substance is used to screen ultraviolet rays in sunlight, a metal oxide having an excellent UV-screening effect such as titanium dioxide or zinc oxide is incorporated into a composition for external use, such as a cosmetic composition, to thereby make use of the UV-screening effect of the metal oxide for protection of the human body from UV rays in sunlight. However, when the metal oxide is used to improve a screening effect against UV-A, whose wavelength range includes a wavelength proximate to the wavelengths of visible light, there arises a problem that the application area of the skin appears unnaturally white due to a characteristic of metal oxides scattering visible light. Therefore, the content of the metal oxide incorporated into a composition for external use is limited. As a result, a composition for external use has not yet led to exerting a sufficient screening effect against UV-A.

At present, measures for screening UV-A have not been fully established.

In view of the foregoing, an object of the present invention is to provide a metal oxide which enables effective UV-screening, i.e., which has excellent screening ability against UV rays, particularly UV-A, as well as excellent transmission with respect to visible light. Another object of the present invention is to provide a UV-screening composition that contains the metal oxide and can be applied to external use.

DISCLOSURE OF THE INVENTION

The present inventors have carried out extensive studies, and have found that zinc oxide that can be produced by a particular method and that has a characteristic form has excellent UV-A-screening ability as well as excellent visible-light transmission. The present invention has accomplished based on this finding.

Accordingly, in the present invention, there is provided zinc oxide in the form of primary particles having an average particle diameter of 50–100 mm and forming a planar shape, the zinc oxide having a ratio represented by $\ln T_{360nm}/\ln T_{400nm}$ ($T_{xnm}$: transmittance of transmitted light of X nm) of 10 or more.

Particularly, there is provided zinc oxide having the following morphological characteristics:

(1) the zinc oxide is in the form of primary particles having an average particle diameter of 50–100 nm and forming a planar shape, the zinc oxide having a roughness corresponding to the diameter of one such primary particle;

(2) the longest dimension of the above zinc oxide is 0.01–5 μm; and (3) the edge portion of the zinc oxide as described in (1) and (2) above has indentures having a depth of 10–200 nm, at intervals of 10–200 nm.

In the present description, the term "the longest dimension" of the zinc oxide is a distance between two points on a plane formed of the zinc oxide primary particles selected such that the distance is maximized.

The zinc oxide according to the present invention (hereinafter referred to as the zinc oxide of the present invention) is produced by crushing the zinc oxide aggregate produced in the following manner.

Specifically, zinc ions ($Zn^{2+}$: supplied by a strong acid salt of zinc such as zinc chloride, zinc sulfate, or zinc nitrate), carbonate ions ($CO_3^{2-}$: supplied by a carbonate salt such as sodium carbonate or potassium carbonate), and hydroxide ions ($OH^-$: supplied by a strong base such as sodium hydroxide or potassium hydroxide) are allowed to react in water, preferably at 40° C.–70° C., while the pH of the aqueous reaction solution is maintained at 7–9 and the mole ratio of hydroxide ion to carbonate ion is fixed to be not greater than 4 (preferably approximately 2.5–3.5, although the amount of hydroxide ion may be 0). Basic zinc carbonate formed in the aqueous reaction solution is calcinated (150° C.–450° C.) to thereby generate the zinc oxide aggregate according to the present invention (hereinafter referred to as "the zinc oxide aggregate of the present invention").

The present invention also provide a UV-screening composition containing the zinc oxide of the present invention that may be applied to a composition for external use such as make-up cosmetics or sunscreen cosmetics, as well as a UV-screening composition containing the zinc oxide aggregate of the present invention.

When the UV-screening composition containing the zinc oxide aggregate is used as a composition for external use, the zinc oxide aggregate contained in the composition is crushed on the skin by friction generated during application of the composition to the skin, to thereby develop, on the skin of the user of the composition, transparency and UV-screening ability induced by the resultant zinc oxide represented by $\ln T_{360nm}/\ln T_{400nm}$ ($T_{xnm}$: transmittance of transmitted light of X nm) of 10 or more.

Thus, the present invention is also directed to a method for use of the external-use composition according to the present invention.

BEST MODE FOR CARRYING OUT THE INVENTION

Figure 1:
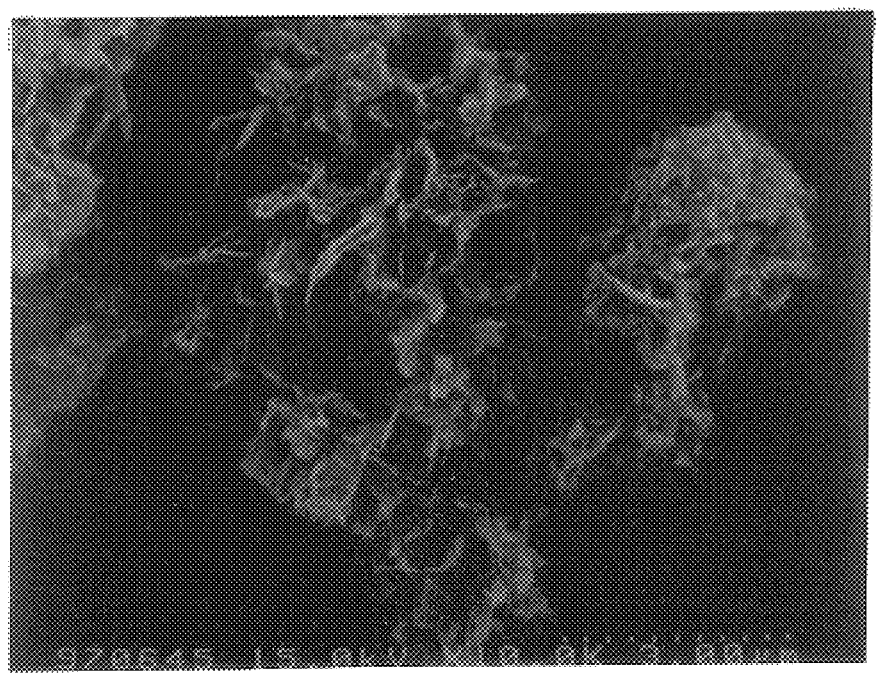
FIG. 1 is a photograph of a metallographic structure of 10000 magnifications showing a zinc oxide aggregate according to the present invention.

The embodiments of the present invention will next be described.

As described above, the zinc oxide of the present invention is zinc oxide in the form of primary particles having an average particle diameter of 50–100 nm and forming a planar shape that has a ratio represented by $\ln T_{360nm}/\ln T_{400nm}$ ($T_{xnm}$: transmittance of transmitted light of X nm) of 10 or more.

In the present invention, the ratio $\ln T_{360nm}/\ln T_{400nm}$ ($T_{xnm}$: transmittance of transmitted light of X nm) with regard to zinc oxide serves as an index to determine whether or not the zinc oxide has the desired characteristics of the present invention.

The ratio $\ln T_{360nm}/\ln T_{400nm}$ represents an index showing the relationship between a screening effect against long-wavelength ultraviolet rays and visible-light transmission. That is, the ratio of the logarithmic transmittance against long-wavelength ultraviolet rays ($\lambda$=360 nm) to the logarithmic transmittance to visible light ($\lambda$=400 nm) makes it possible to simultaneously consider two factors; i.e., transparency and a screening effect against long-wavelength ultraviolet rays.

Accordingly, when zinc oxide has a large value of the ratio $\ln T_{360nm}/\ln T_{400nm}$, the zinc oxide has high transmittance to visible light; i.e., excellent transparency, and also has low transmittance to long-wavelength UV rays; i.e., an excellent screening effect against long-wavelength UV rays.

According to a first aspect of the present invention, there is provided zinc oxide that has a ratio represented by $\ln T_{360nm}/\ln T_{400nm}$ of 10 or more.

No particular limitation is imposed on the general form of the zinc oxide of the present invention so long as the zinc oxide has "a ratio represented by $\ln T_{360nm}/\ln T_{400nm}$ of 10 or more". The zinc oxide of the present invention is zinc oxide consisting of at least one unit of planar zinc oxide when "zinc oxide in the form of primary particles forming one planar shape" is defined as one unit of planar zinc oxide. The below-described "zinc oxide aggregate" differs from the zinc oxide of the present invention in that the zinc oxide of the present invention has a ratio represented by $\ln T_{360nm}/\ln T_{400nm}$ of 10 or more, whereas the zinc oxide aggregate per se has neither a screening effect against long-wavelength UV rays nor visible-light transmission.

The zinc oxide of the present invention is formed in the following manner. First, zinc ions ($Zn^{2+}$), carbonate ions ($CO_3^{2-}$), and hydroxide ions ($OH^-$) are allowed to react in water serving as a solvent while the pH of the aqueous reaction solution is maintained at 7–9 and the mole ratio of hydroxide ion to carbonate ion is fixed to be not greater than 4 (the amount of hydroxide ion may be 0). Basic zinc carbonate formed in the aqueous reaction solution is calcinated to thereby generate a zinc oxide aggregate, which aggregate comprises plural units of the zinc oxide of the present invention, the zinc oxide aggregating together so as to provide the zinc oxide aggregate with microscopic morphology like a carnation (hereinafter, the zinc oxide aggregate is referred to as "the zinc oxide aggregate of the present invention"). The zinc oxide aggregate of the present invention is crushed according to a commonly-used method, to thereby obtain the zinc oxide of the present invention.

Examples of materials that provide the aforementioned zinc ion include zinc salts of strong acid such as zinc chloride, zinc sulfate, and zinc nitrate. Examples of materials that provide the aforementioned carbonate ion include carbonates such as sodium carbonate and potassium carbonate. Examples of materials that provide the aforementioned hydroxide ion include strong bases such as sodium hydroxide and potassium hydroxide.

The basic zinc carbonate formed in the above steps may be produced in such a manner that an aqueous solution in which zinc ion is dissolved and an aqueous solution in which carbonate ion and hydroxide ion are dissolved are mixed so as to maintain the pH of the aqueous reaction solution at 7–9.

The mole ratio of carbonate ion/hydroxide ion is preferably 1/(4 or less) (including the case in which the amount of hydroxide ion is 0). The mole ratio of carbonate/strong base of 1/(2.5–3.5) is particularly preferred.

When the carbonate ion is in excess deviating the above range, unreacted carbonate ions remaining in the reaction solution accumulate. As a result, the microscopic morphology of the formed zinc oxide aggregate results in a card-like or sheet-like form, not a carnation-like form. When such a zinc oxide aggregate is crushed, there might disadvantageously be provided zinc oxide having deteriorated visible-light transmission. When the hydroxide ion is excessive, giant particles having the shape of a grain of rice are generated in the formed zinc oxide aggregate. When such a zinc oxide aggregate is crushed, there might disadvantageously be provided zinc oxide having greatly deteriorated UV-A-screening ability and greatly deteriorated visible-light transmission.

No particular limitation is imposed on the step for forming basic zinc carbonate in the aforementioned aqueous reaction solution so long as carbonate ions are appropriately consumed. As described above, an alkaline solution containing carbonate ions and hydroxide ions and an acidic solution containing zinc ions may be mixed by way of adding dropwise. Alternatively, a solution containing carbonate ions and a solution containing hydroxide ions may be added dropwise separately. Moreover, in consideration of time-course accumulation of carbonate ions in the aqueous reaction solution, the concentration of carbonate ions in the alkaline solution may be gradually decreased in accordance with the accumulation of carbonate ions.

As described above, the pH of the aqueous reaction solution is preferably 7–9. When the pH is in excess of 9, rice-grain-shaped or tetrapod-shaped particles are generated in the formed zinc oxide aggregate. When such a zinc oxide aggregate is crushed, there might disadvantageously be provided zinc oxide having greatly deteriorated UV-A-screening ability and greatly deteriorated visible-light transmission. When the pH is less than 7, efficiency in formation of basic zinc carbonate disadvantageously decreases to a large degree.

The temperature of the aqueous reaction solution is preferably 40–70° C. When the temperature is lower than 40° C., the formation efficiency of basic zinc carbonate decreases; whereas when it is in excess of 70° C., there are generated rice-grain-shaped or tetrahepod-shaped particles which are disadvantageous in that they lead to providing zinc oxide having greatly deteriorated UV-A-screening ability and greatly deteriorated visible-light transmission.

The zinc oxide aggregate of the present invention is formed by calcinating basic zinc carbonate preferably at 150° C.–450° C. When the calcinating temperature is in excess of 450° C., zinc oxide particles are over-sintered to thereby produce a zinc oxide aggregate disadvantageously lacking the desired characteristics of the present invention; whereas when the calcinating temperature is lower than 150° C., decarbonation by calcinating becomes disadvantageously slow with poor practical utilization.

The zinc oxide of the present invention derived from the zinc oxide aggregate of the present invention obtained through calcinating at a lower temperature tends to exert more excellent visible-light transmission. In consideration of the rate of decarbonation reaction, the calcinating temperature is preferably 250° C.–400° C., particularly preferably approximately 250° C.–260° C.

The calcinating time may be selected in accordance with the selected calcinating temperature. For example, when the selected calcinating temperature is low, calcinating is required for a long time (e.g., requiring some days at 150° C.); whereas when the selected calcinating temperature is high, decarbonation is completed by calcinating for a short time (e.g., decarbonation is completed by calcinating for some hours at 250° C.).

There can be obtained the zinc oxide aggregate of the present invention in which a plurality of units of the zinc oxide of the present invention aggregate so as to possess microscopic morphology like a carnation, by calcinating basic zinc carbonate as described above.

Although the microscopic morphology of the zinc oxide aggregate resembles a carnation (c.f., the electron microscopic photographs), the overall morphology of one unit in the aggregate is not limited and varies in accordance with the reaction conditions.

The zinc oxide aggregate of the present invention obtained through the above-described steps is crushed, to thereby produce the zinc oxide of the present invention.

Generally known methods for crushing powder may be employed for crushing the zinc oxide aggregate of the present invention. The zinc oxide aggregate of the present invention may be mechanically crushed to produce the zinc oxide of the present invention. Specific examples of the machines used for crushing include a three-roll mill, an ultrasonic crusher, a bead mill, a motor mill, a ring mill, an atomizer, and a pulverizer. Of these, a three-roll mill and a motor mill are preferred.

Thus, there is provided the zinc oxide of the present invention in the form of primary particles having an average particle diameter of 50–100 nm and forming a planar shape that has a ratio represented by $\ln T_{360nm}/\ln T_{400nm}$ ($T_{xnm}$: transmittance of transmitted light of X nm) of 10 or more.

The zinc oxide of the present invention exerts excellent UV-A-screening ability and visible-light transmission.

The zinc oxide of the present invention has the following morphological characteristics (c.f., the below-mentioned Examples):

(1) the zinc oxide is in the form of primary particles having an average particle diameter of 50–100 n=and forming a planar shape, the planar zinc oxide having a roughness corresponding to the diameter of one such primary particle;

(2) the longest dimension of the above planar zinc oxide is 0.01–5 $\mu$m; and (3) the edge portion of the planar zinc oxide as described in (1) and (2) above has indentures having a depth of 10–200 nm, at intervals of 10–200 nm.

The above-described zinc oxide and zinc oxide aggregate of the present invention may optionally be hydrophobicized and given water repellency through a generally known method for surface-treating. Examples of materials for surface-treating include fatty acid soaps such as aluminum stearate or zinc myristate; waxes such as candelilla wax and carnauba wax; silicones such as methylpolysiloxane and cyclic silicone oil; dextrin fatty acid esters such as dextrin palmitate; and fatty acids such as myristic acid and stearic acid.

The present invention provides a UV-screening composition, which contains the thus-obtained zinc oxide and/or zinc oxide aggregate of the present invention and has a UV-screening effect (hereinafter the UV-screening composition is referred to as the UV-screening composition of the present invention).

The UV-screening composition of the present invention is a composition at least with an intended use of screening (concept including scattering of and absorption of) UV rays. Therefore, no particular limitation is imposed on the embodiment of the composition so long as it is suitable for such a use. Specific examples of the UV-screening compositions include a composition for external use such as cosmetics applied to the skin to thereby protect the human body from UV rays; a resin composition exhibiting a UV-screening effect; and a coating composition which can give a UV-screening effect to an object by coated to the object.

Among the possible embodiments of the UV-screening composition of the present invention, a composition for external use such as a cosmetic composition is particularly preferred in that the zinc oxide of the present invention contained therein as an essential ingredient exerts both excellent UV-screening ability and excellent transparency.

The composition for external use according to the present invention (hereinafter referred to as the composition for external use of the present invention) is described.

The zinc oxide and/or zinc oxide aggregate of the present invention is appropriately incorporated in the composition for external use of the present invention in accordance with the specific form of the composition or other factors. The amount of the zinc oxide and/or zinc oxide aggregate of the present invention in the composition is about 0.001 wt. % or more based on the entirety of the composition, generally 1.0–30.0 wt. %. When the amount is less than 0.001 wt. %, imparting the intended UV-A-screening effect to the composition is difficult.

Although the upper limit of incorporation is about 30.0 wt. % as described above, the limit is merely an index, and the amount of incorporation may be increased to 100 wt. %. As described above, the zinc oxide of the present invention exerts excellent visible-light transmission and excellent transparency. Therefore, when the zinc oxide is incorporated into the composition in a large amount, the composition does not lead to unnaturally white color in application thereof, and can be incorporated in an amount greater than that of conventionally incorporated zinc oxide powder.

Thus, there is provided a composition for external use exhibiting an excellent UV-A-screening effect and excellent transparency at least in application thereof through incorporation of the zinc oxide and/or zinc oxide aggregate of the present invention into the composition.

The composition for external use of the present invention containing the zinc oxide of the present invention shows the above-described excellent UV-A-screening ability and excellent visible-light transmission and excellent transparency even before being applied to the skin.

In contrast, the composition for external use of the present invention containing the zinc oxide aggregate of the present invention hardly exerts the desired effects of the present invention, because the zinc oxide aggregate of the present invention does not have the above-described excellent UW-A-screening ability and excellent visible-light transmission as it is. The above-described effects can be exerted when the composition is actually applied.

In other words, the composition for external use of the present invention containing the zinc oxide aggregate of the present invention imparts transparency and a UV-screening effect to the skin of users induced by the zinc oxide as represented by a $\ln T_{360nm}/\ln T_{400nm}$ ratio ($T_{xnm}$: transmittance of transmitted light of X nm) of 10 or more by crushing the zinc oxide aggregate contained in the composition on the skin through friction generated during application.

As described above, in the present invention, there is also provided a method for use of the composition for external use of the present invention.

To the composition for external use of the present invention, there may be added other ingredients which are usually incorporated into a composition for external use such as a cosmetic composition, so long as the ingredients do not impair the effects of the present invention.

Examples of the ingredients include solid or semi-solid oily components such as vaseline, lanolin, ceresine, carnauba wax, candelilla wax, higher fatty acids, and higher alcohols; liquid oily components such as squalane, liquid paraffin, ester oil, and triglycerides; oily components such as silicone oil; moisturizers such as sodium hyaluronate and glycerin; surfactants such as cationic surfactants and nonionic surfactants; pigments; preservatives; perfumes; activators; and UV-screening agents other than the zinc oxide of the present invention.

The composition for external use of the present invention may be in a form such as powder, cake, pencil, stick, ointment, or liquid. Examples as which the composition of the present invention may be formulated include facial cosmetics such as lotions, milky lotions, and creams; make-up cosmetics such as foundations, lipsticks, eye shadows, cheek rouges, eye liners, nail enamels, and mascaras; hair cosmetics such as hair treatments, hair liquids, and setting lotions; and agents for external use containing-a variety of active ingredients.

Of these, when cosmetics, particularly make-up cosmetics or sunscreen cosmetics which positively screen UV rays in sunlight to thereby prevent sunburn, contain the zinc oxide and/or zinc oxide aggregate of the present invention, they can fully exert the characteristic effects of the present invention; i.e., excellent screening effect against UV rays, particularly long-wavelength UV rays, as well as excellent visible-light transmission, at least during use thereof.

EXAMPLES

The present invention is described in more detail by way of examples, which should not be construed as limiting the invention thereto.

[Production Example] Production of the zinc oxide of the present invention

Sodium carbonate (sodium carbonate decahydrate) and sodium hydroxide in the mole ratios shown in Table 1 were dissolved in 200 ml water, to thereby prepare alkaline solution.

Separately, 1000 ml water was placed in a reaction vessel and heated to 60° C. While the temperature of the aqueous reaction solution was maintained at 60° C. and pH was maintained at 8.0 by use of a pH controller connected to a pump, a 1.0 M aqueous solution of zinc chloride (containing 0.1 M hydrochloric acid) and the above-described alkaline solution were added dropwise to the aqueous reaction solution.

Upon completion of addition of a predetermined amount (see Table 1) of the aqueous solution of zinc chloride, the reaction was stopped. The reaction solution was filtrated through a 0.4 µm filter, followed by washing with water 3 times.

The residue was dried at 150° C. for 12 hours and thereafter calcinated for 2 hours at 400° C., to thereby obtain zinc oxide aggregate of interest.

Next, the resultant zinc oxide aggregate was dispersed in castor oil so as to have a concentration of 40% and pulverized by use of a three-roll mill (EXAKT: Otto Hermann Co. (Germany)), to thereby obtain zinc oxide to be tested.

[Test Example 1]

A. Evaluation of ratio in alkaline solution and morphology of zinc oxide

Each zinc oxide aggregate obtained in the above-mentioned Production Example was observed under a scanning electron microscope at 10,000 or 50,000 magnifications, to thereby evaluate the microscopic morphology of the zinc oxide.

Evaluation Standards

Figure 2:
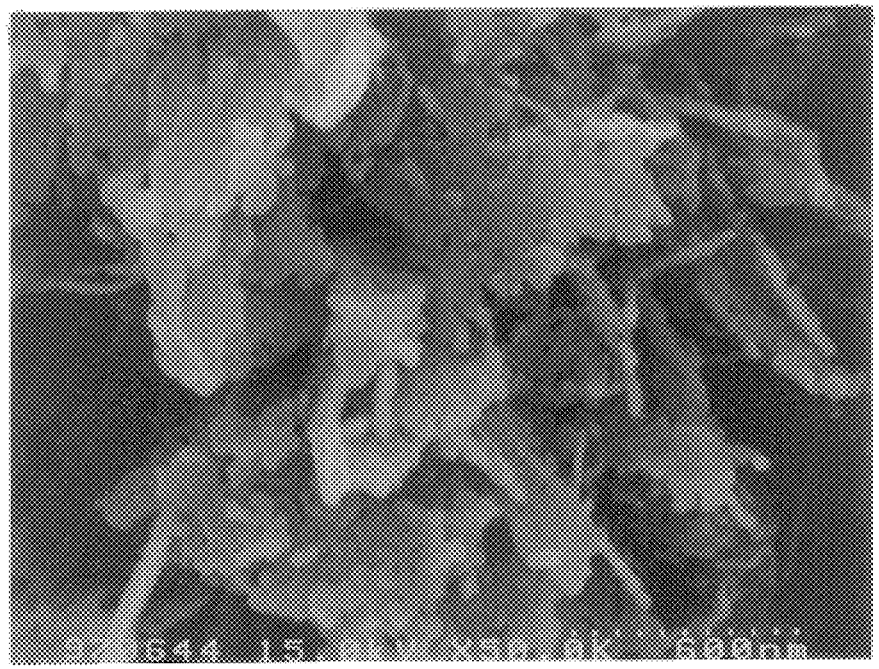
FIG. 2 is a photograph of a metallographic structure of 50000 magnifications showing a zinc oxide aggregate according to the present invention.

◯: Zinc oxide units, each unit of zinc oxide having microscopic morphological characteristics (1)–(3) below, aggregate and the microscopic morphology of the aggregate observed under a microscope resembles a carnation (see FIG. 1: photograph of a metallographic structure of 10000 magnifications, and FIG. 2: photograph of a metallographic structure of 50000 magnifications).

(1) the zinc oxide is in the form of primary particles having an average particle diameter of 50–100 nm and forming a planar shape, the planar zinc oxide having a roughness corresponding to the diameter of one such primary particle;

(2) the longest dimension of the above planar zinc oxide is 0.01–5 μm; and (3) the edge portion of the planar zinc oxide as described in (1) and (2) above has indentures having a depth of 10–200 nm, at intervals of 10–200 nm.

Figure 3:
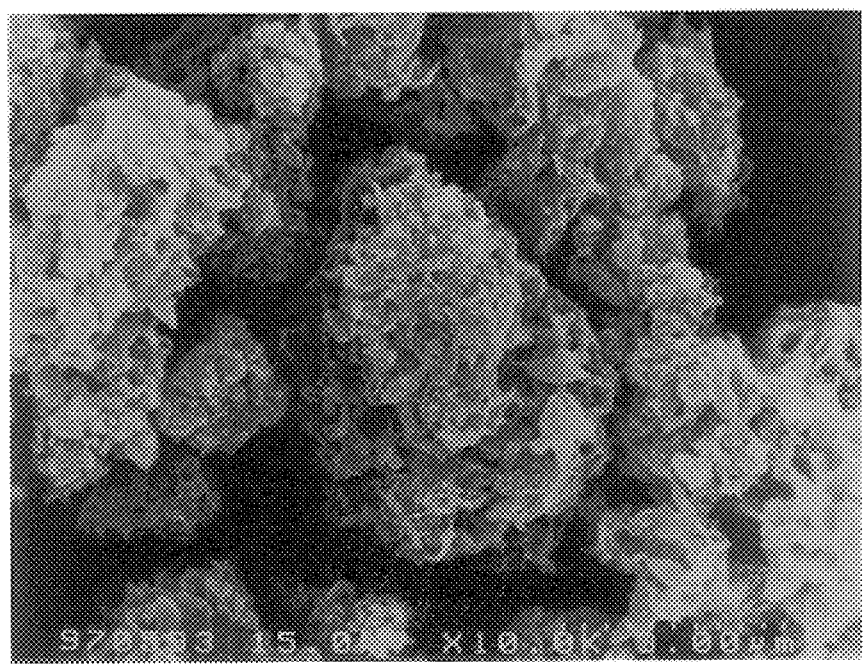
FIG. 3 is a photograph of a metallographic structure of 10000 magnifications showing a zinc oxide aggregate in which giant particles having the shape of a grain of rice are observed.
Figure 4:
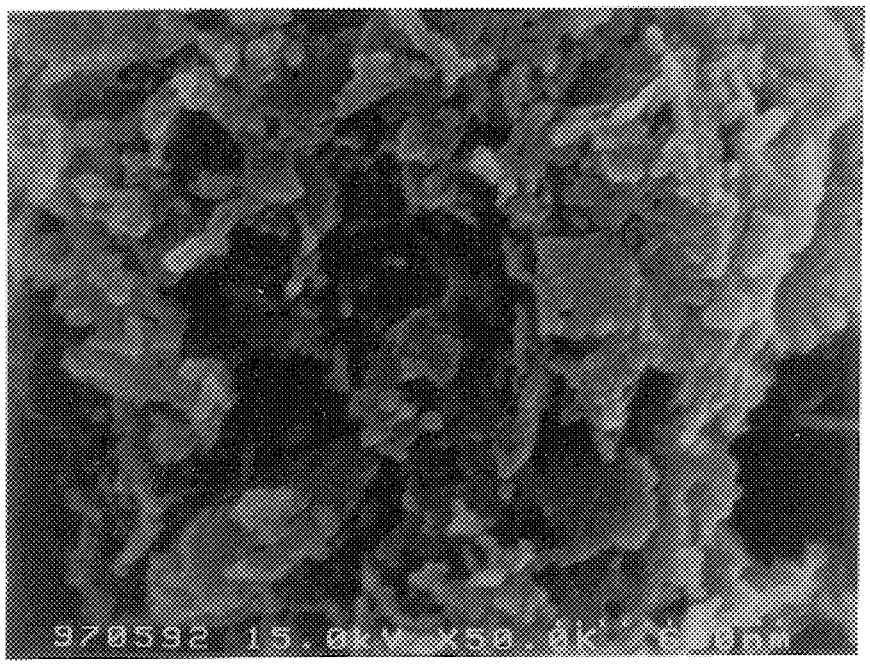
FIG. 4 is a photograph of a metallographic structure of 50000 magnifications showing a zinc oxide aggregate in which giant particles having the shape of a grain of rice are observed.
Figure 5:
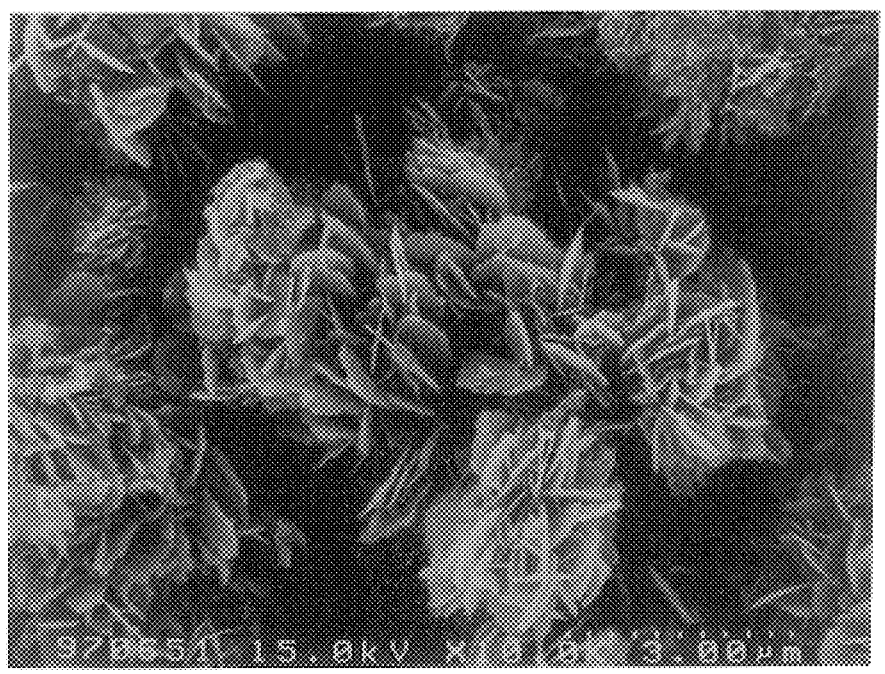
FIG. 5 is a photograph of a metallographic structure of 10000 magnifications showing a zinc oxide aggregate having a card-like shape.
Figure 6:
FIG. 6 is a photograph of a metallographic structure of 50000 magnifications showing a zinc oxide aggregate having a card-like shape.

Δ: Rice-grain-shaped giant particles were observed (see FIG. 3: photograph of a metallographic structure of 10000 magnifications, and FIG. 4: photograph of a metallographic structure of 50000 magnifications).

x: A card-like shape was observed (see FIG. 5: photograph of a metallographic structure of 10000 magnifications, and FIG. 6: photograph of a metallographic structure of 50000 magnifications).

The results are shown in Table 1 (in the Table, "-" denotes "not measured").

TABLE 1

| Ratio in alkaline solution sodium carbonate: sodium hydroxide | Amount of added aqueous solution on zinc chloride | | | | |
|---|---|---|---|---|---|
| (mole ratio) | 20 ml | 40 ml | 100 ml | 500 ml | 1000 ml |
| 1:9 | X | X | X | X | X |
| 1:6 | X | X | X | X | X |
| 1:5 | X | X | X | X | X |
| 1:4 | X | X | X | X | X |
| 1:3.5 | — | — | — | — | O |
| 1:3.25 | — | — | — | O | O |
| 1:3.10 | — | — | — | — | O |
| 1:3.05 | — | — | — | — | O |
| 1:3 | O | O | O | Δ | Δ |
| 1:1 | O | O | X | X | X |
| 4:1 | O | O | X | X | X |
| 7:1 | O | O | X | X | X |
| 1:0 | O | X | X | X | X |

These results suggest that in order to obtain a zinc oxide aggregate of interest having a microscopic morphology of a carnation-like form, the mole ratio of sodium carbonate to sodium hydroxide in an alkaline solution must be 1:(less than 4), and more preferably is 1:2.5–1:3.5.

B. Evaluation of morphology of zinc oxide and relationship between the morphology and light transmission Each zinc oxide sample obtained as described above (obtained by pulverizing the above-mentioned zinc oxide aggregate) was investigated for transmittance of visible light (400 nm) and transmittance of UV-A (360 nm).

The results are shown in Table 2. "Flower-shaped zinc oxide" indicates randomly-sampled zinc oxide obtained by pulverizing zinc oxide aggregate having a carnation-like microscopic morphology. "Card-shaped zinc oxide" indicates randomly-sampled zinc oxide obtained by pulverizing zinc oxide aggregate having a card-like microscopic morphology. "Rice-grain-shaped zinc oxide" indicates randomly-sampled zinc oxide obtained by pulverizing zinc oxide aggregate having rice-grain-shaped giant particles.

Commercial product 1 is ZnO-350 (Sumitomo Osaka Cement Co., Ltd.) and commercial product 2 is FINEX-50 (Sakai Chemical Industry Co., Ltd.)

Transmittance was measured at 400 nm and 360 nm, as described above, by a customary method (a sample thoroughly pulverized in a three-roll mill was dispersed in a dispersion solvent, then appropriately diluted with oil (5–10%), and light transmittance at each wavelength through the dispersion system was measured).

TABLE 2

| | Transmittance at 400 nm | Transmittance at 360 nm | $LnT_{360nm}/lnT_{400nm}$ |
|---|---|---|---|
| Flower-shaped zinc oxide | 90% | 27–32% | 12.42–10.81 |
| Card-shaped zinc oxide | 90% | 37–40% | 9.44–8.70 |
| Rice-grain-shaped zinc oxide | 85% | 40–55% | 5.64–3.68 |
| Commercial product 1 | 90% | 42% | 8.23 |
| Commercial product 2 | 87% | 32% | 8.18 |

The results confirm that the zinc oxide of the present invention prepared from the zinc oxide aggregate of the present invention, whose microscopic morphology resembles a carnation, has more effective UV-A-screening ability and better transmission of visible light; i.e., has better transparency. A value of $lnT_{360nm}/lnT_{400nm}$ ($T_{xnm}$: transmittance of transmitted light of X nm) of the zinc oxide of the present intention is shown to be 10 or more.

Figure 7:
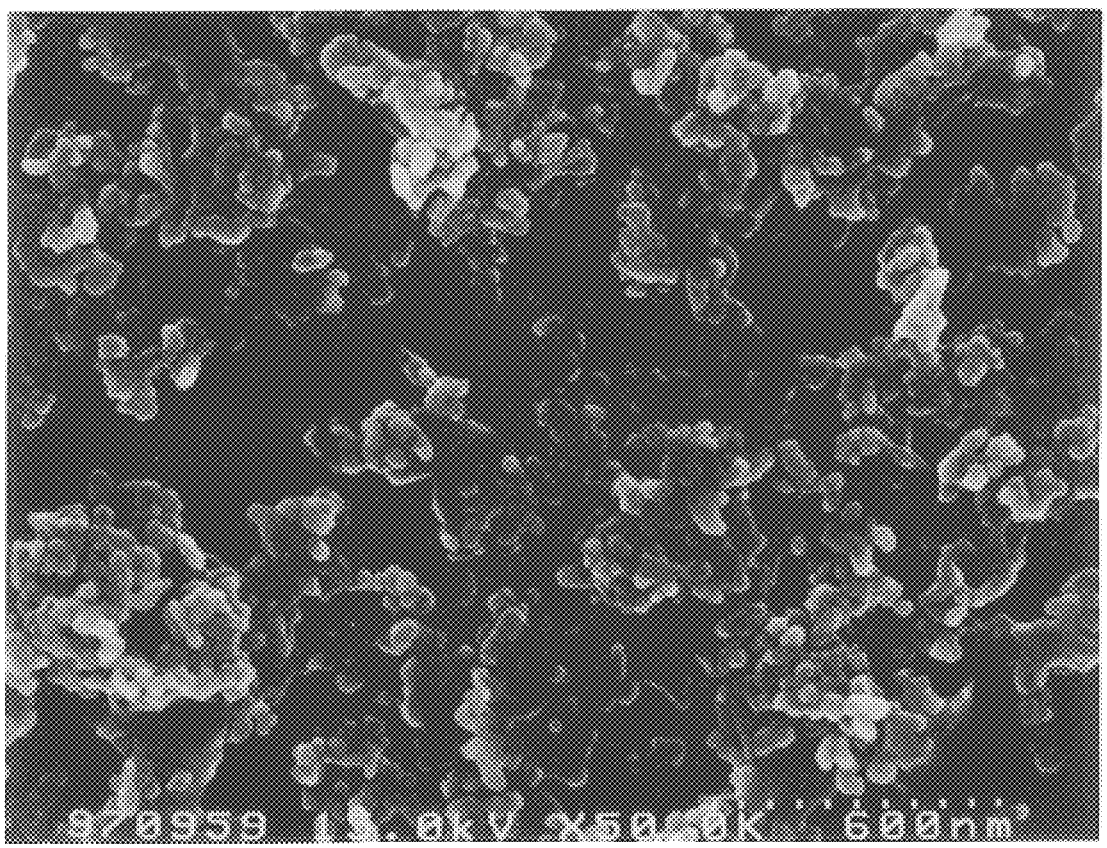
FIG. 7 is a photograph of a metallographic structure of 50000 magnifications showing zinc oxide according to the present invention.

FIG. 7 is a photograph of a metallographic structure (50000 magnifications, under a scanning electron microscope) showing the zinc oxide of the present invention produced by pulverizing the zinc oxide aggregate of the present invention, whose microscopic morphology resembles a carnation, with a three-roll mill. The photograph of the metallographic structure clarifies that zinc oxide of the present invention is in the form of primary particles having an average particle diameter of 50–100 nm and forming a planer shape.

Figure 8:
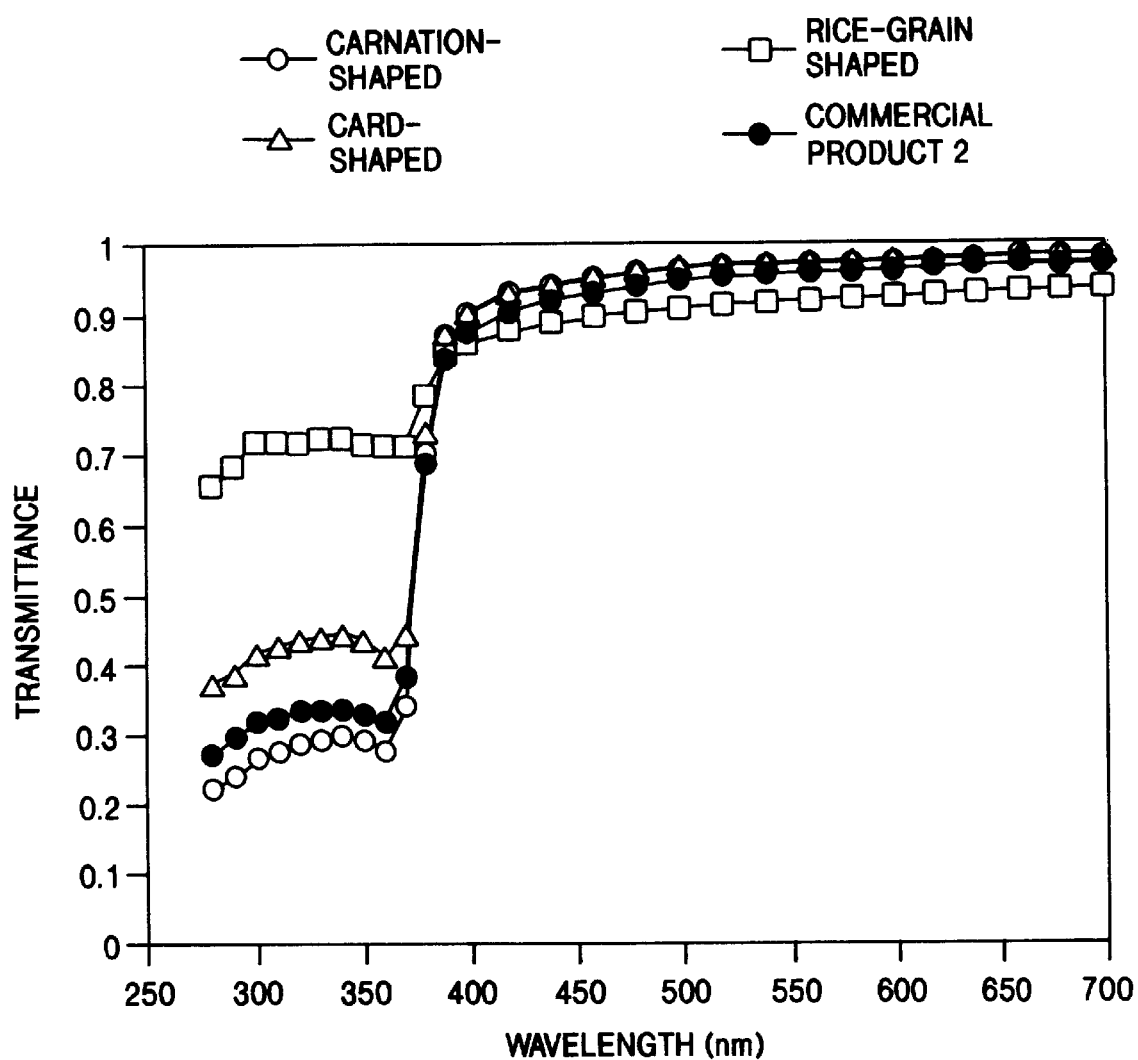
FIG. 8 is a chart confirming transmittance at a variety of wavelengths of zinc oxide according to the present invention and other zinc oxides.

FIG. 8 is a chart showing light transmittance of the zinc oxide of the present invention and that of other types of zinc oxide at different wavelengths, These results show that the zinc oxide of the present invention exhibits a better screening effect against total ultraviolet rays as compared with other zinc oxide, and excellent transmission to visible light, especially to short-wavelength visible light.

C. Relation between calcinating temperature and light transmission

In the above-described Production Example, the mole ratio of sodium carbonate to sodium hydroxide in an alkaline solution was 1 (sodium carbonate): 3.25 (sodium hydroxide) and the quantity of the aqueous solution of zinc chloride was fixed to 1000 ml. Zinc oxide aggregate produced by calcinating at each temperature was pulverized in the above-described manner to thereby obtain zinc oxide. Light transmission of the zinc oxide was evaluated in terms of a ratio of $lnT_{360nm}/lnT_{400nm}$ ($T_{xnm}$: transmittance of transmitted light of X nm). Calcinating was continued until it was proven that a decarbonation reaction had been completed.

The results are shown in Table 3.

TABLE 3

| | 1 | 2 | 3 | 4 | 5 | 6 |
|---|---|---|---|---|---|---|
| Calcinating temp. (° C.) | 150 | 300 | 400 | 500 | 600 | 700 |
| $T_{400nm}$ | 96% | 93% | 90% | 87% | 80% | 80% |
| $T_{360nm}$ | 50% | 38% | 27% | 37% | 45% | 55% |
| $lnT_{360nm}/lnT_{400nm}$ | 16.9 | 13.3 | 12.4 | 7.1 | 3.6 | 2.7 |

In the test system, when the calcinating temperature was in the vicinity of 450° C., the value of $lnT_{360nm}/lnT_{400nm}$ was 10.0. When the calcinating temperature was in excess of 450° C., zinc oxide particles were sintered. In this case, while transmittance to visible light was reduced, screening ability against long-wavelength ultraviolet rays hardly improved and the value of $\ln T_{360nm}/\ln T_{400nm}$ became less than 10.

When the calcinating temperature was set at 150° C., a high value of $\ln T_{360nm}/\ln T_{400nm}$ was obtained. However, in this test system 1, the decarbonation reaction required an entire day for completion, as compared with 1–2 hours in test systems 2 and 3. Therefore a reaction scheme employing a calcinating temperature of 150° C. is disadvantageous in terms of production efficiency.

When a calcinating temperature was set below 150° C., decarbonation reaction required some days for completion and therefore such a temperature is not preferable because production efficiency is considerably deteriorated.

In this test, zinc oxide produced at each calcinating temperature was subjected to X-ray diffraction. A peak indicating zinc oxide produced at low calcinating temperature (150° C.) is broad, indicating that the form of the zinc oxide closely resembles amorphous and that the zinc oxide is excellent in visible-light transmission. Conversely, a peak indicating zinc oxide produced at a calcinating temperature of 400° C. is sharp, indicating that the zinc oxide is excellent in screening effect against long-wavelength ultraviolet rays, although slightly deteriorated in visible-light transmission (the chart is not shown).

The foregoing results prove that, in the preparation of the zinc oxide of the present invention, proper adjustment of calcinating temperature yields zinc oxide having expected light transmission (visible-light transmission and screening effect against long-wavelength ultraviolet rays).

Actual examples of the composition for external use of the present invention (cosmetics) containing the zinc oxide of the present invention obtained in the above-mentioned manner will next be described as Examples (with Comparative Examples). These compositions for external use were prepared in a conventional manner and tested.

In the Examples, "the zinc oxide of the present invention" indicates flower-shaped zinc oxide produced in the above-described Production Example and used in-Test Example 1, and "card-shaped zinc oxide" and "rice-grain-shaped zinc oxide" indicate the respective zinc oxides defined in Test Example 1.

[Example 1] O/W-type Cream

| Ingredient (aqueous phase) | Amount (wt. %) |
| --- | --- |
| purified water | balance |
| 1,3-butylene glycol | 7.0 |
| the zinc oxide of the present invention | 5.0 |
| disodium edetate | 0.05 |
| triethanolamine (99%) | 1.0 |
| (oily phase) | |
| oxybenzone | 2.0 |
| octyl para-methoxycinnamate | 5.0 |
| squalane | 10.0 |
| Vaseline (petrolatum) | 5.0 |
| stearyl alcohol | 3.0 |
| stearic acid | 3.0 |
| glyceryl monostearate | 3.0 |
| polyethyl acryrate | 1.0 |
| antioxidant | suitable amount |
| preservative | suitable amount |
| perfume | suitable amount |

In Comparative Example 1-1, an O/W-type cream was prepared in the same manner as in Example 1 except that the zinc oxide of the present invention was replaced by an equal amount of card-shaped zinc oxide. In Comparative Example 1-2, an O/W-type cream was prepared in the same manner as in Example 1 except that the zinc oxide of the present invention was replaced by an equal amount of rice-grain-shaped zinc oxide. In Comparative Example 1-3, an O/W-type cream was prepared in the same manner as in Example 1 except that the zinc oxide of the present invention was replaced by an equal amount of micro particle titanium dioxide.

[Example 2] O/W-type Milky Lotion

| Ingredient (aqueous phase) | Amount (wt. %) |
| --- | --- |
| purified water | balance |
| dipropylene glycol | 6.0 |
| ethanol | 3.0 |
| hydroxyethylcellulose | 0.3 |
| the zinc oxide of the present invention | 5.0 |
| (oily phase) | |
| octyl para-methoxycinnamate | 6.0 |
| glyceryl octyl para-methoxycinnamate | 2.0 |
| 4-tert-butyl-4'-methoxydibenzoylmethane | 2.0 |
| oxybenzone | 3.0 |
| oleyl oleate | 5.0 |
| dimethyl polysiloxane | 3.0 |
| Vaseline | 0.5 |
| cetyl alcohol | 1.0 |
| sorbitan sesquioleic acid ester | 0.8 |
| polyoxyetylene (20) oleyl alcohol | 1.2 |
| antioxidant | suitable amount |
| preservative | suitable amount |
| perfume | suitable amount |

In Comparative Example 2-1, an O/W-type milky lotion was prepared in the same manner as in Example 2 except that the zinc oxide of the present invention was replaced by an equal amount of card-shaped zinc oxide. In Comparative Example 2-2, an O/W-type milky lotion was prepared in the same manner as in Example 2 except that the zinc oxide of the present invention was replaced by an equal amount of rice-grain-shaped zinc oxide. In Comparative Example 2-3, an O/W-type milky lotion was prepared in the same manner as in Example 2 except that the zinc oxide of the present invention was replaced by an equal amount of micro particle titanium dioxide.

[Example 3] W/O-type Cream

| Ingredient | Amount (wt. %) |
| --- | --- |
| purified water | balance |
| 1,3-butylene glycol | 10.0 |
| (oily phase) | |
| the zinc oxide of the present invention (hydrophobicized) | 20.0 |
| squalane | 20.0 |
| glyceryl diisostearate | 5.0 |
| organically modified montmorillonite | 3.0 |
| preservative | suitable amount |
| perfume | suitable amount |

In Comparative Example 3-1, a W/O-type cream was prepared in the same manner as in Example 3 except that the zinc oxide of the present invention was replaced by an equal amount of card-shaped zinc oxide which had been hydrophobicized. In Comparative Example 3-2, a W/O-type cream was prepared in the same manner as in Example 3 except that the zinc oxide of the present invention was replaced by an equal amount of rice-grain-shaped zinc oxide which had been hydrophobicized. In Comparative Example 3-3, a W/O-type cream was prepared in the same manner as in Example 3 except that the zinc oxide of the present invention was replaced by an equal amount of commercially available zinc oxide (FINEX-50, product of Sakai Chemical Industry Co., Ltd.) which had been hydrophobicized.

[Example 4] Oily Cosmetic Composition

| Ingredient | Amount (wt. %) |
|---|---|
| the zinc oxide of the present invention | 10.0 |
| liquid paraffin | 60.0 |
| cetyl octanoate | 28.0 |
| antioxidant | suitable amount |
| perfume | suitable amount |

In Comparative Example 4-1, an oily cosmetic composition was prepared in the same manner as in Example 4 except that the zinc oxide of the present invention was replaced by an equal amount of card-shaped zinc oxide. In Comparative Example 4-2, an oily cosmetic composition was prepared in the same manner as in Example 4 except that the zinc oxide of the present invention was replaced by an equal amount of rice-grain-shaped zinc oxide. In Comparative Example 4-3, an oily cosmetic composition was prepared in the same manner as in Example 4 except that the zinc oxide of the present invention was replaced by an equal amount of commercially available zinc oxide (FINEX-50, product of Sakai Chemical Industry Co., Ltd.).

[Example 5] Oily Cosmetic Composition

| Ingredient | Amount (wt. %) |
|---|---|
| the zinc oxide of the present invention (hydrophobicized) | 10.0 |
| liquid paraffin | 48.0 |
| isopropyl myristate | 10.0 |
| silicone oil | 30.0 |
| silicone resin | 2.0 |
| antioxidant | suitable amount |
| perfume | suitable amount |

In Comparative Example 5-1, an oily cosmetic composition was prepared in the same manner as in Example 5 except that the zinc oxide of the present example was replaced by an equal amount of card-shaped zinc oxide which had been hydrophobicized. In Comparative Example 5-2, an oily cosmetic composition was prepared in the same manner as in Example 5 except that the zinc oxide of the present invention was replaced by an equal amount of rice-grain-shaped zinc oxide which had been hydrophobicized. In Comparative Example 5-3, an oily cosmetic composition was prepared in the same manner as in Example 5 except that the zinc oxide of the present invention was replaced by an equal amount of commercially available zinc oxide (FINEX-50, product of Sakai Chemical Industry Co., Ltd.) which had been hydrophobicized.

[Example 6] Gel

| Ingredient | Amount (wt. %) |
|---|---|
| the zinc oxide of the present invention | 10.0 |
| liquid paraffin | 60.0 |
| olive oil | 20.0 |
| organically modified montmorillonite | 5.0 |
| BHT (antioxidant) | suitable amount |
| perfume | suitable amount |

In Comparative Example 6-1, a gel was prepared in the same manner as in Example 6 except that the zinc oxide of the present invention was replaced by an equal amount of card-shaped zinc oxide. In Comparative Example 6-2, a gel was prepared in the same manner as in Example 6 except that the zinc oxide of the present invention was replaced by an equal amount of rice-grain-shaped zinc oxide. In Comparative Example 6-3, a gel was prepared in the same manner as in Example 6 except that the zinc oxide of the present invention was replaced by an equal amount of commercially available zinc oxide (FINEX-50, product of Sakai Chemical Industry Co., Ltd.).

[Example 7] Lotion

| Ingredient | Amount (wt. %) |
|---|---|
| purified water | balance |
| the zinc oxide of the present invention | 5.0 |
| dipropylene glycol | 5.0 |
| 1,3-butylene glycol | 10.0 |
| polyethylene glycol 400 | 10.0 |
| ethyl alcohol | 20.0 |
| polyoxyethylene (60) hydrogenated castor oil | 3.0 |
| octyl para-methoxycinnamate | 1.0 |
| perfume | suitable amount |

In Comparative Example 7-1, a lotion was prepared in the same manner as in Example 7 except that the zinc oxide of the present invention was replaced by an equal amount of card-shaped zinc oxide. In Comparative Example 7-2, a lotion was prepared in the same manner as in Example 7 except that the zinc oxide of the present invention was replaced by an equal amount of rice-grain-shaped zinc oxide. In Comparative Example 7-3, a lotion was prepared in the same manner as in Example 7 except that the zinc oxide of the present invention was replaced by an equal amount of commercially available zinc oxide (FINEX-50, product of Sakai Chemical Industry Co., Ltd.).

[Example 8] Two-Way Foundation

| Ingredient | Amount (wt. %) |
|---|---|
| silicone-treated talc | 19.2 |
| silicone-treated mica | 40.0 |
| the zinc oxide of the present invention (hydrophobicized) | 5.0 |
| silicone-treated titanium dioxide | 15.0 |
| red iron oxide treated with silicone | 1.0 |
| yellow iron oxide treated with silicone | 3.0 |
| black iron oxide treated with silicone | 0.2 |
| zinc stearate | 0.1 |
| nylon powder | 2.0 |

-continued

| Ingredient | Amount (wt. %) |
| --- | --- |
| squalane | 4.0 |
| solid paraffin | 0.5 |
| dimethylpolysiloxane | 4.0 |
| glyceryl triisooctanoate | 5.0 |
| octyl methoxycinnamate | 1.0 |
| preservative | suitable amount |
| antioxidant | suitable amount |
| perfume | suitable amount |

In Comparative Example 8-1, a two-way foundation was prepared in the same manner as in Example 8 except that the zinc oxide of the present invention was replaced by an equal amount of card-shaped zinc oxide which had been hydrophobicized. In Comparative Example 8-2, a two-way foundation was prepared in the same manner as in Example 8 except that the zinc oxide of the present invention was replaced by an equal amount of rice-grain-shaped zinc oxide which had been hydrophobicized. In Comparative Example 8-3, a two-way foundation was prepared in the same manner as in Example 8 except that the zinc oxide of the present invention was replaced by an equal amount of commercially available zinc oxide (FINEX-50, product of Sakai Chemical Industry Co., Ltd.) which had been hydrophobicized.

[Example 9] Cake-type Foundation

| Ingredient | Amount (wt. %) |
| --- | --- |
| talc | 36.9 |
| kaolin | 15.0 |
| sericite | 10.0 |
| zinc flower | 7.0 |
| the zinc oxide of the present invention | 10.0 |
| red iron oxide | 1.0 |
| yellow iron oxide | 2.9 |
| black iron oxide | 0.2 |
| squalane | 8.0 |
| POE sorbitan monooleate | 3.0 |
| isocetyl octanoate | 2.0 |
| isostearic acid | 4.0 |
| preservative | suitable amount |
| antioxidant | suitable amount |
| perfume | suitable amount |

In Comparative Example 9-1, a cake-type foundation was prepared in the same manner as in Example 9 except that the zinc oxide of the present invention was replaced by an equal amount of card-shaped zinc oxide. In Comparative Example 9-2, a cake-type foundation was prepared in the same manner as in Example 9 except that the zinc oxide of the present invention was replaced by an equal amount of rice-grain-shaped zinc oxide. In Comparative Example 9-3, a cake-type foundation was prepared in the same manner as in Example 9 except that the zinc oxide of the present invention was replaced by an equal amount of commercially available zinc oxide (FINEX-50, product of Sakai Chemical Industry Co., Ltd.).

[Example 10] O/W Emulsified-type Foundation (liquid-type)

| Ingredient | Amount (wt. %) |
| --- | --- |
| talc | 3.0 |
| the zinc oxide of the present invention | 15.0 |
| red iron oxide | 0.5 |
| yellow iron oxide | 1.4 |
| black iron oxide | 0.1 |
| bentonite | 0.5 |
| polyoxyethylene sorbitan monostearate | 0.9 |
| triethanolamine | 1.0 |
| propylene glycol | 10.0 |
| purified water | balance |
| stearic acid | 2.2 |
| isohexadecyl alcohol | 7.0 |
| glyceryl monostearate | 2.0 |
| liquid lanolin | 2.0 |
| liquid paraffin | 2.0 |
| preservative | suitable amount |
| perfume | suitable amount |

In Comparative Example 10-1, an O/W emulsified-type foundation (liquid-type) was prepared in the same manner as in Example 10 except that the zinc oxide of the present invention was replaced by an equal amount of card-shaped zinc oxide. In Comparative Example 10-2, an O/W emulsified-type foundation (liquid-type) was prepared in the same manner as in Example 10 except that the zinc oxide of the present invention was replaced by an equal amount of rice-grain-shaped zinc oxide. In Comparative Example 10-3, an O/W emulsified-type foundation (liquid-type) was prepared in the same manner as in Example 10 except that the zinc oxide of the present invention was replaced by an equal amount of commercially available zinc oxide (FINEX-50, product of Sakai Chemical Industry Co., Ltd.).

[Example 11] O/W Emulsified-type Foundation (cream-type)

| Ingredient | Amount (wt. %) |
| --- | --- |
| hydrophobicized sericite | 5.36 |
| hydrophobicized kaolin | 4.0 |
| the zinc oxide of the present invention (hydrophobicized) | 9.32 |
| hydrophobicized red iron oxide | 0.36 |
| hydrophobicized yellow iron oxide | 0.8 |
| hydrophobicized black iron oxide | 0.16 |
| liquid paraffin | 5.0 |
| decamethylcyclopentasiloxane | 12.0 |
| polyoxyethylene-modified dimethylpolysiloxane | 4.0 |
| purified water | balance |
| dispersing agent | 0.1 |
| 1,3-butylene glycol | 5.0 |
| preservative | suitable amount |
| stabilizer | 2.0 |
| perfume | suitable amount |

In Comparative Example 11-1, an O/W emulsified-type foundation (cream-type) was prepared in the same manner as in Example 11 except that the zinc oxide of the present invention was replaced by an equal amount of card-shaped zinc oxide which had been hydrophobicized. In Comparative Example 11-2, an O/W emulsified-type foundation (cream-type) was prepared in the same manner as in Example 11 except that the zinc oxide was replaced by an equal amount of rice-grainshaped zinc oxide which had been hydrophobicized. In Comparative Example 11-3, an O/W emulsified-type foundation (cream-type) was prepared in the same manner as in Example 11 except that the zinc oxide of the present invention was replaced by an equal amount of commercially available zinc oxide (FINEX-50, product of Sakai Chemical Industry Co., Ltd.) which had been hydrophobicized.

[Example 12] W/O Emulsified-type Foundation (two-phase-dispersion-type)

| Ingredient | Amount (wt. %) |
|---|---|
| hydrophobicized talc | 7.0 |
| the zinc oxide of the present invention (hydrophobicized) | 12.0 |
| silicic anhydride | 2.0 |
| nylon powder | 4.0 |
| coloring pigment | 2.0 |
| octamethylcyclotetrasiloxane | 10.0 |
| pentaerythritol rosinate | 1.5 |
| neopentyl glycol diisooctanoate | 5.0 |
| squalane | 2.5 |
| glyceryl triisooctanoate | 2.0 |
| polyoxyethylene-modified dimethylpolysiloxane | 1.5 |
| purified water | balance |
| 1,3-butylene glycol | 4.0 |
| ethanol | 7.0 |

In Comparative Example 12-1, a W/O emulsified-type foundation (two-phase-dispersion type) was prepared in the same manner as in Example 12 except that the zinc oxide of the present invention was replaced by an equal amount of card-shaped zinc oxide which had been hydrophobicized. In Comparative Example 12-2, a W/o emulsified-type foundation (two-phase-dispersion type) was prepared in the same manner as in Example 12 except that the zinc oxide of the present invention was replaced by an equal amount of rice-grain-shaped zinc oxide which had been hydrophobicized. In Comparative Example 12-3, a W/O emulsified-type foundation (two-phase-dispersion-type) was prepared in the same manner as in Example 12 except that the zinc oxide of the present invention was replaced by an equal amount of commercially available zinc oxide (FINEX-50, product of Sakai Chemical Industry Co., Ltd.) which had been hydrophobicized.

[Example 13] Powdery Foundation

| Ingredient | Amount (wt. %) |
|---|---|
| talc | 20.3 |
| mica | 30.0 |
| kaolin | 5.0 |
| the zinc oxide of the present invention | 10.0 |
| titanium dioxide | 5.0 |
| zinc stearate | 1.0 |
| red iron oxide | 1.0 |
| yellow iron oxide | 3.0 |
| black iron oxide | 0.2 |
| nylon powder | 10.0 |
| squalane | 6.0 |
| lanolin acetate | 1.0 |
| octyldodecyl myristate | 2.0 |
| neopentyl glycol diisooctanoate | 2.0 |
| sorbitan monooleate | 0.5 |
| preservative | suitable amount |
| perfume | suitable amount |

In Comparative Example 13-1, a powdery foundation was prepared in the same manner as in Example 13 except that the zinc oxide of the present invention was replaced by an equal amount of card-shaped zinc oxide. In Comparative Example 13-2, a powdery foundation was prepared in the same manner as in Example 13 except that the zinc oxide of the present invention was replaced by an equal amount of rice-grain-shaped zinc oxide. In Comparative Example 13-3, a powdery foundation was prepared in the same manner as in Example 13 except that the zinc oxide of the present invention was replaced by an equal amount of commercially available zinc oxide (FINEX-50, product of Sakai Chemical Industry Co., Ltd.).

[Test Example 2] Evaluation of compositions for external use (cosmetic composition)

A. Evaluation based on a value of $\ln T_{360nm}/\ln T_{400nm}$

Each cosmetic composition was formed into a 5 μm-thick film on a quartz plate. For each of these measurement samples, transmittance at λ=360 nm serving as an evaluation index of screening effect against long-wavelength ultraviolet rays and transmittance at λ=400 nm serving as an evaluation index of visible-light transmission were measured by use of a spectrophotometer (Hitachi UV3410, integrating-sphere mounted). Based on these data, $\ln T_{360nm}/\ln T_{400nm}$ was calculated and Examples 1–7 (along with related Comparative Examples) were evaluated.

Evaluation standards
○: $\ln T_{360nm}/\ln T_{400nm}$ is not less than 10
Δ: $\ln T_{360nm}/\ln T_{400nm}$ is less than 10 and not less than 8
×: $\ln T_{360}/\ln T_{400nm}$ is less than 8
The results are shown in Table 4.

TABLE 4

| | transmittance (λ = 400 nm) | transmittance (λ = 360 nm) | Evaluation |
|---|---|---|---|
| Example 1 | 90 (%) | 27 (%) | ○ |
| Comparative Example 1-1 | 87 | 25 | Δ |
| Comparative Example 1-2 | 85 | 60 | × |
| Comparative Example 1-3 | 84 | 21 | Δ |
| Example 2 | 88 | 23 | ○ |
| Comparative Example 2-1 | 87 | 25 | Δ |
| Comparative Example 2-2 | 85 | 60 | × |
| Comparative Example 2-3 | 85 | 25 | Δ |
| Example 3 | 91 | 31 | ○ |
| Comparative Example 3-1 | 87 | 31 | Δ |
| Comparative Example 3-2 | 85 | 59 | × |
| Comparative Example 3-3 | 87 | 31 | Δ |
| Example 4 | 87 | 22 | ○ |
| Comparative Example 4-1 | 87 | 31 | Δ |
| Comparative Example 4-2 | 85 | 60 | × |
| Comparative Example 4-3 | 85 | 27 | Δ |
| Example 5 | 87 | 21 | ○ |
| Comparative Example 5-1 | 87 | 30 | Δ |
| Comparative Example 5-2 | 85 | 60 | × |
| Comparative Example 5-3 | 84 | 21 | Δ |
| Example 6 | 90 | 27 | ○ |
| Comparative Example 6-1 | 87 | 25 | Δ |
| Comparative Example 6-2 | 85 | 60 | × |
| Comparative Example 6-3 | 84 | 21 | Δ |
| Example 7 | 87 | 21 | ○ |
| Comparative Example 7-1 | 87 | 25 | Δ |
| Comparative Example 7-2 | 85 | 60 | × |
| Comparative Example 7-3 | 84 | 21 | Δ |

As shown in Table 4, whether the zinc oxide of the present invention was hydrophobicized or not, all the cosmetic compositions containing the zinc oxide of the present invention exhibited a $\ln T_{360nm}/\ln T_{400nm}$ value of not less than 10, and all the Comparative Examples exhibited a $\ln T_{360nm}/\ln T_{400nm}$ value of less than 10.

In other words, cosmetic compositions containing the zinc oxide of the present invention exhibit desired characteristics; e.g., excellent visible-light transmission and excellent screening effect against long-wavelength ultraviolet rays.

B. Evaluation based on transmittance at λ=360 nm

For cosmetic compositions of Examples 8–13 (including related Comparative Examples), only transmittance at λ=360 nm, which relates to screening effect against long-wavelength ultraviolet rays, was used as the evaluation index. (The measurement method was the same as described above in "A.")

Evaluation standards
○: $T_{360nm}$ a value is less than 30%
Δ: $T_{360nm}$ value is at least 30% and less than 40%
×: $T_{360nm}$ value is at least 40%

The results are shown in Table 5.

TABLE 5

|  | Transmittance (λ = 360 nm) | Evaluation |
| --- | --- | --- |
| Example 8 | 21 (%) | ○ |
| Comparative Example 8-1 | 25 | ○ |
| Comparative Example 8-2 | 30 | Δ |
| Comparative Example 8-3 | 20 | ○ |
| Example 9 | 22 | ○ |
| Comparative Example 9-1 | 25 | ○ |
| Comparative Example 9-2 | 42 | × |
| Comparative Example 9-3 | 21 | ○ |
| Example 10 | 27 | ○ |
| Comparative Example 10-1 | 31 | Δ |
| Comparative Example 10-2 | 40 | × |
| Comparative Example 10-3 | 24 | ○ |
| Example 11 | 24 | ○ |
| Comparative Example 11-1 | 29 | ○ |
| Comparative Example 11-2 | 55 | × |
| Comparative Example 11-3 | 24 | ○ |
| Example 12 | 24 | ○ |
| Comparative Example 12-1 | 29 | ○ |
| Comparative Example 12-2 | 36 | Δ |
| Comparative Example 12-3 | 22 | ○ |
| Example 13 | 24 | ○ |
| Comparative Example 13-1 | 29 | ○ |
| Comparative Example 13-2 | 34 | Δ |
| Comparative Example 13-3 | 24 | ○ |

As is apparent from Table 5, all the cosmetic compositions containing the zinc oxide of the present invention were evaluated as being equal or superior to the most excellent Comparative Example in terms of screening effect against long-wavelength ultraviolet rays.

In other words, the zinc oxide of the present invention, even if contained in a foundation which poses no direct problems in visible-light transmission, exhibits a screening effect against long-wavelength ultraviolet rays equal or superior to that of the most effective conventional zinc oxide.

Industrial Applicability

As described above, the present invention provides zinc oxide having an excellent screening effect, particularly against long-wavelength ultraviolet rays (UV-A), and further provides a UV-screening composition; e.g., a composition for external use, which contains the zinc oxide of the present invention and has an excellent screening effect against ultraviolet rays and excellent transparency.

What is claimed is:

1. Zinc oxide which is in the form of a plurality of primary particles each having an average particle diameter of 50–100 nm and said plurality of primary particles forming a planar shape, and which has a ratio of the natural logarithm of the transmittance of long-wavelength ultraviolet rays (Γ=360 nm) to the logarithm of the transmittance of visible light (Γ=400 nm) is 10 or more.

2. Zinc oxide according to claim 1, wherein:
    (a) the zinc oxide has a roughness corresponding to the diameter of one such primary particle;
    (b) the longest dimension of the zinc oxide is 0.01–5 μm; and
    (c) the edge portion of the zinc oxide has indentures having a depth of 10–200 nm, at intervals of 10–200 nm.

3. Zinc oxide aggregate formed from the zinc oxide of claim 1, wherein the zinc oxide aggregates together to resemble a carnation as shown in the photograph, FIG. 1.

4. Zinc oxide aggregate according to claim 3, obtainable by reacting zinc ions ($Zn^{2+}$), carbonate ions ($CO_3^{2-}$), and hydroxide ions ($OH^-$) in water, while the pH of the aqueous reaction solution is maintained at 7–9 and the mole ratio of hydroxide ion to carbonate ion is fixed to be not greater than 4 (including the case in which the amount of hydroxide ion is 0), and calcinating basic zinc carbonate formed in the aqueous reaction solution at a temperature of 150–450° C.

5. Zinc oxide aggregate according to claim 4, wherein the mole ratio of hydroxide ion to carbonate ion is 2.5–3.5.

6. Zinc oxide aggregate according to claim 4, wherein, in the aqueous reaction solution, 1) the zinc ions are provided by zinc chloride, zinc sulfate, or zinc nitrate; 2) the carbonate ions are provided by sodium carbonate or potassium carbonate; and 3) the hydroxide ions are provided by sodium hydroxide or potassium hydroxide.

7. Zinc oxide aggregate according to claim 4, wherein the temperature of the aqueous reaction solution is 40° C.–70° C.

8. Zinc oxide, obtained by crushing the zinc oxide aggregate as described in claim 3.

9. A UV-screening composition containing the zinc oxide as described in claim 1.

10. A UV-screening composition according to claim 9, which is a composition for external use.

11. A UV-screening composition according to claim 10, wherein the composition for external use is make-up cosmetics.

12. A UV-screening composition according to claim 10, wherein the composition for external use is sunscreen cosmetics.

13. An external-use composition comprising the zinc oxide aggregate as described in claim 3.

14. An external-use composition according to claim 13, which is make-up cosmetics.

15. An external-use composition according to claim 13, which is sunscreen cosmetics.

16. A method for use of an external-use composition as described in claim 13, which comprises applying to skin the external-use composition to generate a frictional force; allowing the frictional force to crush the zinc oxide aggregate on the skin; and developing, on the skin, transparency and UV-screening ability of the zinc oxide expressed by the ratio of the natural logarithm of the transmittance of long-wavelength ultraviolet rays (Γ=360 nm) to the natural logarithm of the transmittance of visible light (Γ=400 nm) of 10 or more.

17. Zinc oxide aggregate wherein the zinc oxide as described in claim 2 aggregates together.

18. Zinc oxide aggregate according to claim 5, wherein, in the aqueous reaction solution, 1) the zinc ions are provided by zinc chloride, zinc sulfate, or zinc nitrate; 2) the carbonate ions are provided by sodium carbonate or potassium carbonate; and 3) the hydroxide ions are provided by sodium hydroxide or potassium hydroxide.

19. Zinc oxide aggregate according to claim 5, wherein the temperature of the aqueous reaction solution is 40° C.–70° C.

20. Zinc oxide aggregate according to claim 6, wherein the temperature of the aqueous reaction solution is 40° C.–70° C.

21. Zinc oxide, obtained by crushing the zinc oxide aggregate as described in claim 3.

22. Zinc oxide, obtained by crushing the zinc oxide aggregate as described in claim 4.

23. Zinc oxide obtained by crushing the zinc oxide aggregate as described in claim 5.

24. Zinc oxide obtained by crushing the zinc oxide aggregate as described in claim 6.

25. Zinc oxide obtained by crushing a zinc oxide aggregate as described in claim 17.

26. Zinc oxide obtained by crushing a zinc oxide aggregate as described in claim 17 which is formed by causing a reaction between zinc ions ($Zn^{2+}$), carbonate ions ($CO_3^{2-}$), and hydroxide ions ($OH^-$) in water, while the pH of the aqueous reaction solution is maintained at 7–9 and the mole ratio of hydroxide ion to carbonate ion is fixed to be not greater than 4 (including the case in which the amount of hydroxide ion is 0), and calcinating basic zinc carbonate formed in the aqueous reaction solution.

27. Zinc oxide according to claim 26 wherein said reaction is carried out with a mole ratio of hydroxide ion to carbonate ion of 2.5–3.5.

28. Zinc oxide according to claim 27 wherein in the aqueous reaction solution, 1) the zinc ions are provided by zinc chloride, zinc sulfate, or zinc nitrate; 2) the carbonate ions are provided by sodium carbonate or potassium carbonate: and 3) the hydroxide ions are provided by sodium hydroxide or potassium hydroxide.

29. Zinc oxide according to claim 28 wherein the temperature of the aqueous reaction solution is 40° C–70° C.

30. An external-use composition comprising the zinc oxide aggregate as described in claim 4.

31. An external-use composition comprising the zinc oxide aggregate as described in claim 5.

32. An external-use composition comprising the zinc oxide aggregate as described in claim 6.

33. An external-use composition comprising the zinc oxide aggregate as described in claim 7.

34. A v-screening composition containing the zinc oxide as described in claim 1.

35. A UV-screening composition according to claim 11, wherein the composition for external use is sunscreen cosmetics.

36. An external-use composition according to claim 14, which is a sunscreen cosmetic.

37. The method for use of an external-use composition according to claim 16, wherein said external-use composition is a make-up cosmetic.

38. The method for use of an external-use composition according to claim 16, wherein said external-use composition is a Sunscreen cosmetic.

* * * * *